United States Patent
Rangachari et al.

(10) Patent No.: US 6,310,268 B1
(45) Date of Patent: Oct. 30, 2001

(54) NON-IONIC PLASTICIZER ADDITIVES FOR WOOD PULPS AND ABSORBENT CORES

(75) Inventors: Krishnakumar Rangachari, Savannah; Kays Chinai, St. Simons Island, both of GA (US)

(73) Assignee: Rayonier Products and Financial Services Company, Ferandina Beach, FL (US)

( * ) Notice: Subject to any disclaimer, the term of this patent is extended or adjusted under 35 U.S.C. 154(b) by 0 days.

(21) Appl. No.: 09/642,862

(22) Filed: Aug. 21, 2000

Related U.S. Application Data

(63) Continuation-in-part of application No. 09/408,047, filed on Sep. 29, 1999.

(51) Int. Cl.$^7$ .................................................... A61F 13/15
(52) U.S. Cl. ..................... 604/375; 264/116; 264/122; 264/518; 162/158
(58) Field of Search .................. 264/518, 115, 264/116, 122; 162/158; 604/375

(56) References Cited

U.S. PATENT DOCUMENTS

| | | | |
|---|---|---|---|
| 2,249,118 | 7/1941 | De Witt . | |
| 3,554,862 | 1/1971 | Hervey et al. | 162/158 |
| 3,677,886 | 7/1972 | Forssblad et al. | 162/72 |
| 3,809,604 | 5/1974 | Estes et al. | 162/100 |
| 4,144,122 | 3/1979 | Emanuelsson et al. | 162/158 |
| 4,303,471 | 12/1981 | Kemi | 162/158 |
| 4,432,833 | 2/1984 | Breese | 162/158 |
| 4,583,980 | 4/1986 | Schneider et al. | 604/359 |
| 4,610,678 | 9/1986 | Weisman et al. | 604/368 |
| 5,516,569 | 5/1996 | Veith et al. | 428/68 |
| 5,547,541 | 8/1996 | Hansen et al. | 162/12 |
| 5,641,561 | 6/1997 | Hanson et al. | 442/417 |
| 5,695,486 | 12/1997 | Broughton et al. | 604/374 |
| 5,776,308 | 7/1998 | Sears et al. | 162/158 |
| 5,837,627 | 11/1998 | Halabisky et al. | 442/385 |
| 5,858,172 | 1/1999 | Sears et al. | 162/158 |
| 5,866,242 | 2/1999 | Tan et al. | 428/219 |
| 5,916,670 | 6/1999 | Tan et al. | 428/219 |
| 5,935,880 | 8/1999 | Wang et al. | 442/65 |

FOREIGN PATENT DOCUMENTS

| | | |
|---|---|---|
| WO 99/24667 | 5/1999 | (WO) . |
| WO 00/36215 A1 | 6/2000 | (WO) . |

*Primary Examiner*—Mary Lynn Theisen
(74) *Attorney, Agent, or Firm*—Rockey, Milnamow & Katz, Ltd.

(57) ABSTRACT

Soft wood pulp sheets, soft absorbent cores, and methods for making the soft wood pulp sheets or soft absorbent cores by addition of non-ionic plasticizers before, during or after the pulp or core manufacturing process are disclosed. Preferred non-ionic plasticizers are ethers or esters such as triacetin, citrates or glycol derivatives.

34 Claims, No Drawings

NON-IONIC PLASTICIZER ADDITIVES FOR WOOD PULPS AND ABSORBENT CORES

CROSS-REFERENCE TO RELATED APPLICATIONS

This application is a continuation-in-part of co-pending U.S. patent application Ser. No. 09/408,047 filed Sep. 29, 1999.

FIELD OF THE INVENTION

This invention is directed to soft wood pulp sheets, soft absorbent cores, and methods for making the soft wood pulp sheets or soft absorbent cores by addition of non-ionic plasticizers before, during or after the pulp or core manufacturing process. Preferred non-ionic plasticizers are ethers or esters such as triacetin, citrates or glycol derivatives.

BACKGROUND OF THE INVENTION

A wide variety of absorbent structures for use in disposable absorbent articles are known in the art. Common commercial absorbent articles include diapers, adult incontinence products, catamenials and bandages. These products are provided with various functional components for receiving, absorbing and retaining fluids.

Disposable absorbent articles, such as diapers, feminine hygiene products, adult incontinence devices and the like have found widespread acceptance. To function efficiently, such absorbent articles must quickly absorb body fluids, distribute those fluids within and throughout the absorbent article and be capable of retaining those body fluids with sufficient energy to dry the surface when placed under loads. In addition, the absorbent article need be sufficiently soft and flexible so as to comfortably conform to body surfaces and provide close fit for lower leakage.

While the design of individual absorbent articles varies depending upon use, there are certain elements or components common to such articles. The absorbent article contains a liquid pervious top sheet or facing layer, which facing layer is designed to be in contact with a body surface. The facing layer is made of a material that allows for the unimpeded transfer of fluid from the body into the core of the article. The facing layer should not absorb fluid per se and, thus, should remain dry. The article further contains a liquid impervious back sheet or backing layer disposed on the outer surface of the article and which layer is designed to prevent the leakage of fluid out of the article.

Disposed between the facing layer and backing layer is an absorbent member referred to in the art as an absorbent core. The function of the absorbent core is to absorb and retain body fluids entering the absorbent article through the facing layer. Because the origin of body fluids is localized, it is necessary to provide a means for distributing fluid throughout the dimensions of the absorbent core to make full use of all the available absorbent material. This is typically accomplished either by providing a distribution member disposed between the facing layer and absorbent core and/or altering the composition of the absorbent core per se.

Fluid can be distributed to different portions of the absorbent core by means of a transfer or acquisition layer disposed between the facing layer and core. Because of the proximity of such an acquisition layer to the body surface of the wearer, the acquisition layer should not be formed from material that retains large amounts of fluid. The purpose of the acquisition layer is to provide for rapid transfer and distribution of fluid to the absorbent core while minimizing spread of the fluid in this layer.

The absorbent core is typically formulated of a cellulosic wood fiber matrix or pulp, which pulp is capable of absorbing large quantities of fluid. Absorbent cores can be designed in a variety of ways to enhance fluid absorption and retention properties. By way of example, the fluid retention characteristics of absorbent cores can be greatly enhanced by disposing superabsorbent materials amongst fibers of the wood pulp. Superabsorbent materials are well known in the art as substantially water-insoluble, absorbent polymeric compositions that are capable of absorbing large amounts of fluid in relation to their weight and forming hydrogels upon such absorption. Absorbent articles containing blends or mixtures of pulp and superabsorbents are known in the art.

The distribution of superabsorbents within an absorbent core can be uniform or non-uniform. By way of example, that portion of an absorbent core proximate to the backing layer (farthest away from the wearer) can be formulated to contain higher levels of superabsorbent than those portions of the core proximate the facing or acquisition layer. By way of further example, that portion of the core closest to the site of fluid entry (e.g., acquisition zone) can be formulated to transport (wick) fluid into surrounding portions of the core (e.g., storage zone).

As consumer demand for less expensive and less bulky disposable absorbent products increases, manufacturers continue to seek effective ways to reduce size and cost without sacrificing the quality of the fluid transport properties or structural integrity of the products during use. Preferably, the disposable products should be soft, thin and absorbent. Unfortunately, when softness and thinness characteristics are improved through the use of additives known in the art, absorbency is sacrificed. Therefore, there is a need in the industry for manufacturing processes which produce a soft and thin material while maintaining the desired level of absorbency.

Absorbent materials, such as absorbent cores may be made from pulp in the form of sheets or board. The pulp is defiberized in order to manufacture an absorbent material. Therefore, additives which improve the characteristics of the absorbent end product may be added 1) to the pulp, 2) during the manufacture of pulp board, or 3) during manufacture of the absorbent core. Conventionally, for the manufacture of absorbent materials, softness is achieved by the addition of debonders to the pulp, since the softness of a pulp product is greatly influenced by the degree to which the constituent wood pulp is debonded, i.e., the extent to which hydrogen bonds within the wood pulp are broken. For example. debonder is added to the pulp while the pulp is in the holding chests, prior to deposition of the pulp slurry on the Fourdrinier wire. The result is softer pulps or pulp products, which typically have decreased hydrogen bonding.

Wood pulp softness can be expressed in terms of properties such as Mullen strength (the strength of pulp or a pulp product, measured in kilopascals (kPa), defined in greater detail below), and Kamas energy (the energy required to convert a given amount of pulp or pulp product to a fluff material, measured in watt hours per kilogram (Wh/kg), defined in greater detail below). Lower values of Mullen strength and Kamas energy correlate to softer, increasingly debonded, pulp.

Many industrial pulp applications involve the conversion of pulp to fluff pulp by mechanical means. The efficient mechanical fluffing of wood pulp requires a pulp (stiff) that will debond to a desirable degree with minimum energy input and little mechanical fiber damage. Such pulp must have the proper bulk and degree of inter-fiber bonding. A hard pulp sheet will increase the energy needed to create fluff pulp and will therefore lead to increased fiber damage, while an unduly soft pulp sheet will lead to pull-out of large pieces of pulp, causing poor fluffing.

Currently, cationic compounds are used in the manufacture of wood pulp products such as sanitary papers to yield a product which has a soft hand feel. This is accomplished through the lubricating nature of the substantive softening molecule; less extensive inter-fiber bonding leading to greater bulk and the plasticizing effect of these additives.

There are several cationic chemical materials known for use to soften pulp to produce a fluff or debonded pulp. These cationic materials are quaternary ammonium compounds, as disclosed in U.S. Pat. Nos. 3,554,862; 3,677,886; 3,809,604; 4,144,122 and 4,432,833 among others.

Nonionic agents are also used to a limited extent to debond pulp in the paper industry (BEROCELL 587, available from Eka Nobel) but even they cause adverse affects on absorbency. It is believed that this effect is due to the presence of long hydrophobic side chains.

Water-soluble polyhydroxy alcohols have been disclosed as softening agents in U.S. Pat. No. 2,249,118. Non-ionic compounds such as fatty acid esters in combination with cationic retention agents have been disclosed in U.S. Pat. No. 4,303,471 to obtain good disintegration properties for pulp.

However, pulp softening and debonding, when accomplished by the conventional treatments described above, will result in a material that is less absorbent.

As an alternative to the use of additives, materials may be specifically engineered to obtained the desired characteristics. In addition to blending pulp with superabsorbent material, a variety of other means for improving the characteristics of pulp have been described.

One particular desirable character is the stiffness of the absorbent core. As the disposable hygiene products industry moves towards ultrathin products, stiffness of the absorbent core has become a critical issue. The use of mercerized fibers to reduce the stiffness (or improve the softness) of absorbent cores has been disclosed in U.S. Pat. No. 5,866,242. However these fibers arc expensive when compared to non-mercerized fibers.

Debonding agents such as quaternary ammonium compounds can be used to produce soft pulp sheets and absorbent cores. However, as previously mentioned, the use of debonders result in a substantial negative impact on absorbency.

There have been numerous attempts by the manufacturers of absorbent materials to produce core materials which arc highly absorbent, strong, and soft U.S. Pat. No. 4,610,678 discloses an air-laid material containing hydrophilic fibers and superabsorbent material, wherein the material is air-laid in a dry state and compacted without the use of any added binding agents. Such material, however, has low integrity and suffers from shake-out or loss of substantial amounts of superabsorbent material. U.S. Pat. No. 5,516,569 discloses that superabsorbent material shake-out can be reduced in air-laid absorbents by adding significant amounts of water to material during the air-laying process. The resultant material, however, is stiff of low density and has a high water content (>about 15 weight percent). The high stiffness can be reduced using embossing which requires an additional processing step in the manufacturing process, but embossing has been shown to have a negative impact on the tensile strength of the core. Thus, use of the above steps to produce soft absorbent cores results in substantial increases in the cost of the core.

For example, soft absorbent materials are disclosed in U.S. Pat. Nos. 5,866,242 and 5,916,670. However, the processes disclosed therein may be expensive, so it would be desirable to use an additive which would provide a lower cost alternative, if such additive could be used to treat pulps to provide beneficial properties to pulp, and thereafter to absorbent cores formed from treated pulps, without decreasing absorbency.

There continues to be a need in the art, therefore, for a material that satisfies the absorbency, strength and softness requirements needed for use as absorbent core in disposable absorbent articles and which simultaneously provides time and cost savings to both the pulp manufacturer and the manufacturer of the absorbent article.

Accordingly, it would be desirable to provide a method of treating pulp sheets to form fluff pulp with improved softness without sacrificing the absorbent properties of the pulp.

SUMMARY OF THE INVENTION

One aspect of the invention is an absorbent core comprising from 0.1% to 10% of at least one non-ionic plasticizer. The plasticizer may be a citrate or triacetin; the core may have a suppleness of greater than about 0.7 $g^{-1}$; a density of from about 0.25 g/cc to about 0.5 g/cc; and a basis weight of from about 200 $g/m^2$ to about 550 $g/m^2$.

Another aspect of the invention is an absorbent core comprising:
  from about 30 weight percent to about 90 weight percent of cellulosic fibers; and,
  from about 0.1 weight percent to about 10 weight percent of at least one non-ionic plasticizer;
  wherein said core has a suppleness of greater than about 0.7 $g^{-1}$; a density of from about 0.25 g/cc to about 0.5 g/cc and a basis weight of from about 200 $g/m^2$ to about 550 $g/m^2$.

Examples of suitable plasticizers are esters or ethers. The ethers or esters may be glycol derivatives, and the esters may also be citrates. Suitable glycol ethers include alkyl ethers of low molecular weight glycols or aryl ethers of low molecular weight glycols. Suitable glycol esters include formic esters of low molecular weight glycols, ethanoic esters of low molecular weight glycols or propanoic esters of low molecular weight glycols. A preferred ester is triacetin. Preferred citrates are of the formula

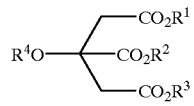

wherein $R^1$, $R^2$ and $R^3$ are each independently alkyl groups, and
  $R^4$ is selected from the group consisting of hydrogen, alkyl groups and $—C(O)R^5$, wherein $R^5$ is an alkyl group. The plasticizer may be triacetin. Cellulosic fibers used to make the cores may be derived from at least one type of pulp sheet, or from a mixture of at least two types of pulp sheets. The core may further comprise from about 9.99 weight percent to about 60 weight percent of superabsorbent polymer. When the core contains superabsorbent polymer, the core may have a normalized wicking energy greater than about 2,300 ergs/g.

Another aspect of the invention is a method for manufacturing a softened absorbent material from cellulosic fibers comprising the steps of:

a) defiberizing cellulosic fibers to form defiberized cellulosic fibers;

b) blending said defiberized cellulosic fibers with super-absorbent material to form a blended material;

c) depositing said blended material onto a carrier layer under vacuum to form a layered absorbent web; and d) compressing said web to form an absorbent material, wherein an effective softening amount of at least one non-ionic plasticizer is added to at least one of said cellulosic fibers, said defiberized cellulosic fibers, said blended material, said web and said absorbent material.

The absorbent material may be an absorbent core. If the plasticizer is anti-microbial, the softened absorbent wood pulp product is an anti-microbial, softened, absorbent wood pulp product. If the plasticizer is odor-preventing, the softened absorbent wood pulp product is an odor-preventing, softened absorbent wood pulp product.

Suitable plasticizers are as defined above. The cellulosic fibers used to make the cores may be derived from at least one type of pulp sheet, or from a mixture of at least two types of pulp sheets.

Another aspect of the invention is a wood pulp sheet comprising:

from about 90 weight percent to about 99.9 weight percent of cellulosic fibers; and, from about 0.1 weight percent to about 10 weight percent of at least one citrate, wherein said sheet has a defiberization energy of from about 35 to about 60 Wh/kg.

Suitable citrates are as defined above. Presently preferred wood pulp sheets have a wicking energy greater than about 40,000 ergs/g, and more preferably greater than about 60,000 ergs/g.

Another aspect of the invention is a method for softening wood pulp sheets comprising the step of adding to said sheets an effective wood pulp sheet softening amount of at least one citrate of the formula

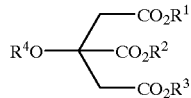

wherein $R^1$, $R^2$ and $R^3$ are each independently alkyl groups, and $R^4$ is selected from the group consisting of hydrogen, alkyl groups and —$C(O)R^5$, wherein $R^5$ is an alkyl group.

Suitable citrates are as defined above.

DETAILED DESCRIPTION OF THE INVENTION

Definitions

The term "non-ionic plasticizer" as used herein refers to compounds such as esters or ethers. The ethers or esters may be glycol derivatives, and the esters may also be citrates. Suitable glycol ethers include alkyl ethers of low molecular weight glycols or aryl ethers of low molecular weight glycols. Suitable glycol esters include formic esters of low molecular weight glycols, ethanoic esters of low molecular weight glycols or propanoic esters of low molecular weight glycols. A preferred ester is triacetin. One or more non-ionic plasticizers may be added, as combinations of non-ionic plasticizers may increase the efficacy of the desired result.

The term "citrate" as used herein refers to compounds of general formula I,

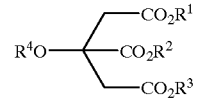

Formula I wherein $R^1$, $R^2$ and $R^3$ are each independently alkyl groups (each may be different, or all may be the same), and $R^4$ is selected from the group consisting of hydrogen, alkyl groups and —$C(O)R^5$, wherein $R^5$ is an alkyl group.

The term "alkyl" as used herein alone or in combination refers to $C_1$–$C_{12}$ straight or branched, saturated or unsaturated (alkenyl, alkynyl, allyl) chain radicals derived from saturated hydrocarbons by the removal of one hydrogen atom. Representative examples of alkyl groups include methyl, ethyl, n-propyl, iso-propyl, n-butyl, sec-butyl, iso-butyl, and tert-butyl among others.

The term "aryl" as used herein alone or in combination refers to a carbocyclic aromatic group having about 6 to 12 carbon atoms such as phenyl, naphthyl, indenyl, indanyl, azulenyl, fluorenyl and anthracenyl.

The term "wood pulp" as used herein refers to a cellulosic material obtained from wood produced according to a pulping process including but not limited to sulfite, kraft and thermomechanical pulping processes, and in which lignin and other cellulose pulp impurities may be removed in whole or in part by a process which includes but is not limited to an oxidation or other bleaching process, wherein cellulosic hydroxyl groups naturally present in the cellulosic material have not been chemically substituted or derivatized. Cellulose ether and acetate end-use derivative products are not considered wood pulp.

The term "softened pulps" refers to fibrous end-use wood pulps (for example, fluff pulps) that have some chemical agent (softener) added to soften the pulp, preferably by reducing interfiber bonding (addition of the softener results in a soft pulp sheet). The chemical agents (softeners) are commercial products added to fluff pulps during sheet forming which make the pulp sheet softer and easier to fluff or defiber. The force with which pulp fibers bond is measured indirectly by measuring Mullen strength or the force (or energy) expended to debond or fluff a given pulp sheet.

As used herein, the term "cellulosic fibers" refers to those fibers which are conventionally employed to form a web for use, for example, in absorbent articles. A wide variety of pulped cellulosic fibers, derived from wood and non-wood sources, can be used. Cellulosic fibers that can be used in the present invention are well known in the art and include wood pulp, cotton, flax and peat moss. Wood pulp is preferred. Cellulose acetate fibers are not included in this definition. Pulps and cores of the present invention are cellulose acetate-free. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present invention. Wood pulp is most commonly employed because of its availability and price. Therefore, cellulosic fibers derived primarily from wood pulp are most preferred.

Suitable wood pulp fibers for use with the invention can be obtained from well-known chemical processes. The pulp fibers may also be processed by chemical methods, thermo-mechanical methods, chemithermomechanical methods, or combinations thereof. The preferred pulp fiber is produced by chemical methods, either sulfate or sulfite. The preferred starting material is prepared from long-fiber coniferous wood species such as southern pine, Douglas fir, spruce, and hemlock. Other chemical pulps made from short or long fibered wood species, ground wood fibers, recycled or secondary wood pulp fibers, and bleached and unbleached wood pulp fibers can be used. Short wood fibers are produced from hardwood species, such as eucalyptus, using known chemical processes or from any wood species using mechanical or chemithermomechanical methods. Details of the production of wood pulp fibers are well-known to those skilled in the art.

The term "wood pulp sheet" as used herein refers to cellulosic fiber sheets formed using the wet-laid process. The sheets typically have a basis weight of between 200 and 800 gsm and density between 0.3 to 1.0 g/cc. The pulp sheets are subsequently defibered in a hammermill to convert them into fluff pulp before being used in an absorbent product. Wood pulp sheets can be differentiated from tissue paper or paper sheets by their basis weights. Typically, tissue paper has a basis weight of from about 5 to about 50 gsm and paper sheets have basis weights of from about 47 to about 103 gsm. Therefore, these materials have lower basis weights than wood pulp sheets.

The term "absorbent core" as used herein refers to a cellulosic wood fiber matrix or pulp, which pulp is capable of absorbing large quantities of fluid. Absorbent cores can be designed in a variety of ways to enhance fluid absorption and retention properties. By way of example, the fluid retention characteristics of absorbent cores can be greatly enhanced by disposing superabsorbent materials amongst fibers of the wood pulp. The absorbent core may be used to manufacture consumer products such as diapers, feminine hygiene products or incontinence products.

Superabsorbent materials are well-known to those skilled in the art as substantially water-insoluble, absorbent polymeric compositions that are capable of absorbing large amounts of fluid in relation to their weight and forming hydrogels upon such absorption.

The terms "superabsorbent polymer" or "SAP" as used herein refer to a polymeric material that is capable of absorbing large quantities of fluid by forming a hydrated gel. The superabsorbent polymers also can retain significant amounts of water under moderate pressures. Superabsorbent polymers generally fall into three classes, namely, starch graft copolymers, cross-linked carboxymethylcellulose derivatives, and modified hydrophilic polyacrylates. Examples of such absorbent polymers are hydrolyzed starch-acrylonitrile graft copolymer; a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-cross-linking polyacrylic acid, a cross-linked polyacrylate salt, carboxylated cellulose, and a neutralized cross-linked isobutylene-maleic anhydride copolymer. An absorbent material of the present invention can contain any SAP known in the art. The SAP can be in the form of particulate matter, flakes, fibers and the like. Exemplary particulate forms include granules, pulverized particles, spheres, aggregates and agglomerates. Exemplary and preferred SAPs include salts of crosslinked polyacrylic acid such as sodium polyacrylate.

The term "Mullen strength" as used herein refers to the hydrostatic pressure, typically measured in kilopascals, required to produce rupture of a material under certain experimental conditions. Mullen strength is determined on some of the products presented in the examples using a method based on TAPPIT807. A TMI Monitor Burst 1000 is used to measure the hydrostatic pressure required to rupture a pulp sheet. Mullen strength is recorded as kPa at rupture.

The term "Kamas energy" as used herein refers to the energy required to convert a given amount of pulp or pulp product to a fluff material measured in watt hours per kilogram (Wh/kg). A Kamas lab hammer mill Model H-01-C was used to defiberize some of the products presented in the examples. Strips of pulp sheets 5 cm wide and having a basis weight of 640 gsm were fed into the hammermill, using, 4200 rpm motor speed, 50% feeder speed, and an 8 mm screen. The energy required to defiberize the pump sheet is recorded, and reported as Wh/kg of fluff, the energy of defiberization.

The Gurley stiffness values of the absorbent materials were measured using a Gurley stiffness tester (Model No 4171E), manufactured by Gurley Precision Instruments of Troy, N.Y. The instrument measures the externally applied moment required to produce a given deflection of a test strip of specific dimensions fixed at one end and having a concentrated load applied to the other end. The results are obtained in "Gurley stiffness" values in units of milligrams. It should be noted that the higher the stiffness of the material, the less flexible and hence the less soft it is.

The Methods

One aspect of this invention is a method for obtaining a softened absorbent core by adding a plasticizer as a softener to the process stream at any convenient point in the air-laid manufacturing process. The process stream contains wood pulp as well as other additives. Production of an absorbent material by air-laying means is well known in the art. Briefly, cellulosic fibers (e.g., pulp) are processed using a hammermill to individualize the fibers. The individualized fibers are blended with SAP granules in a blending system and pneumatically conveyed into a series of forming heads. The blending and distribution of absorbent materials can be controlled separately for each forming head. Controlled air circulation and winged agitators in each chamber produce uniform mixture and distribution of pulp and SAP. The SAP can be thoroughly and homogeneously blended throughout the web or contained only in specific strata by distributing it to selected forming heads. Fibers (and SAP) from each forming chamber are deposited by vacuum onto a carrier layer, thus forming a layered absorbent web. The web is subsequently compressed using calenders to achieve desirable density. The deified web is wound into a roll using conventional winding equipment. A forming wire can be covered with tissue paper to reduce the loss of material as the carrier layer. The tissue paper layer can be removed prior to calendering or incorporated into the formed material.

Moreover, an absorbent core having improved properties may be obtained by post-manufacturing application of additive, by applying the additive to the core which results from the air-laid process described above.

Another aspect of this invention relates to the treatment of wood pulp sheets useful for making a fluff pulp preferably for absorbency intensive applications. Surprisingly, this method of treating wood pulp sheets with a softening agent to soften the pulp does not adversely effecting the absorbency of the material. The wood pulp sheet is treated by applying to the wood pulp sheet a sufficient amount of a material comprising the softening agent.

Various types of wood pulp sheets were tested to measure the effect that the softening agents of the present invention had on properties including Mullen strength, Kamas energy, absorption time and fluid retention. It was found that citrate esters reduce Kamas energy, reduce Mullen strength, and have a negligible effect on both absorption time and fluid retention properties of pulp sheets.

When the invention is practiced industrially, the softening agents are best applied to wood pulp sheets in an aqueous solution which can be made up in a holding tank or prepared continuously with an in-line static mixer. In the manufacture of absorbent pulp sheets, these agents can be added to a fiber slurry at the machine chest, fan pump or head box. They can also be applied by spray application to a wet pulp sheet or can be applied via a "dip and nip" procedure in which an evacuated but not completely dried pulp sheet is dipped into a solution containing the agent and subsequently pressed. Additionally, softening agents of the invention may be sprayed, rolled or printed onto one or both sides of a pulp sheet.

The wood pulp used in the sheets treated by the methods of the present invention can also be pretreated prior to use with the present invention. This pretreatment may include physical treatment, such as subjecting the fibers to steam, or chemical treatment, for example, cross-linking the cellulose fibers using any of a variety of cross-linking agents such as dimethyl dihydroxyethylene urea. Cross-linking the fibers, for example, increases their resiliency, and thereby can improve their absorbency. The fibers may also be twisted or crimped, as desired.

Although not to be construed as a limitation, examples of pretreating fibers include the application of fire retardants to the fibers, such as by spraying the fibers with fire-retardant chemicals. Specific fire-retardant chemicals include, by way of example, sodium borate/boric acid, urea, and urea/phosphates. In addition, the fibers may be pre-treated with surfactants or other liquids, such as water or solvents, which modify the surface of the fibers. These are known as softened or debonded fibers. Other pre-treatments include exposure to antimicrobials, pigments and densification or softening agents. Fibers pre-treated with other chemicals, such as thermoplastic and thermosetting resins also may be used.

Wood pulp sheets may be treated for softening by spraying the softener on the sheet as it is rolled up upon formation in the papermaking process, or by spraying the softener as the rolled sheets of pulp are unrolled for further processing. Sheets so treated, when utilized to make an absorbent core, results in a softer absorbent core which retains capacity for liquid retention.

The Additives

Plasticizers such as tributyl citrate have been used in combination with terpolymers to form binder compositions to make soft absorbent webs which are capable of dispersing in an aqueous environment into unrecognizable pieces in U.S. Pat. No. 5,935,880. These binder compositions of the '880 patent are used by those skilled in the art as additives in the wet laid process, for manufacturing absorbent materials having basis weights below 125. For the present invention, absorbent cores are manufactured by an air-laid process, which is utilized to make materials having much higher basis weights.

Citric acid has been disclosed as a binder useful in combination with a densifying agent to bind particles to fibers in U.S. Pat. Nos. 5,641,561 and 5,547,541. However, citric acid is not a plasticizer, as it is a carboxylic acid, while art recognized plasticizers are esters or ethers. Additionally, citric acid esters have been used for odor-prevention in sanitary hygiene products as disclosed in U.S. Pat. No. 4,583,980. In the '980 patent, a high concentration of additive (12.5–37.5%) is utilized to create an additive layer in the product. By contrast, the present invention utilizes much lower concentrations.

Triacetin has been used as a solvent for a bonding medium such as cellulose acetate to form a strengthened web containing pulped cellulosic fibers as disclosed in U.S. Pat. Nos. 5,837,627 and 5,695,486. However, when these materials are strengthened using a combination of cellulose acetate and triacetin, absorbency decreases. In the present invention, cellulose acetate is not contemplated to be within the definition of cellulosic fibers.

Triacetin was first recognized to provide softening in pulp in U.S. Pat. Nos. 5,776,308 and 5,858,172. These patents also disclosed other non-ionic compounds such as alkyl ethers, aryl ethers, formic, ethanoic and propanoic esters of low molecular weight glycols (such as propylene glycol diacetate and 2-phenoxyethanol) for softening wood pulp. However, the citrate esters of the present invention have not been disclosed for such purposes. Moreover, the use of these non-ionic compounds as additives in the manufacture of absorbent cores has not previously been disclosed.

Examples of suitable plasticizers are esters or ethers. The ethers or esters may be glycol derivatives, and the esters may also be citrates or triacetin. Suitable glycol ethers include alkyl ethers of low molecular weight glycols or aryl ethers of low molecular weight glycols. Suitable glycol esters include formic esters of low molecular weight glycols, ethanoic esters of low molecular weight glycols or propanoic esters of low molecular weight glycols.

Examples of suitable citrate esters include trimethyl citrate, acetyl trimethyl citrate, triethyl citrate, tri-n-butyl citrate, acetyl triethyl citrate, acetyl tri-n-butyl citrate, acetyl tri-n-hexyl citrate, n-butyryl tri-n-hexyl citrate, acetyl tri-n-(hexyl/octyl/decyl) citrate and acetyl tri-n-(octyl/decyl) citrate and combinations thereof among others.

Addition of the plasticizers of the present invention should not decrease the relative liquid absorption rate of said absorbent material by more than 5%.

Compounds are preferably added neat, though it should be noted that application of a softening agent to wood pulp is not limited to neat application, and can also include application in solution, as an emulsion, as a suspension or a dispersion. One or more of the additives described above may be utilized. Plasticizers may act synergistically with each other. Moreover, other additives which may be used in conjunction with the non-ionic plasticizers of the present invention include absorbent capacity enhancing materials such as superabsorbent polymers, zeolites and activated carbon, brighteners such as titanium dioxide, and odor absorbents such as sodium bicarbonate, EDTA, zeolites, activated carbon and borates. Solvents can also reduce the dusting caused by the additives or the pulp itself because more of the fines are attached and bound to the matrix by the bonding medium.

The effective softening amount of the additives described above will depend upon the system to be treated. Factors which will influence how much of the additive is necessary include the type of wood pulp utilized, particular processing conditions, which other additives are present, which particular additive is selected and the desired properties of the resultant absorbent core.

Test Procedures & Definitions

In the tests described hereinafter, industry-employed standard test procedures have been used. If any deviations from standard test procedure have been made, such deviations have been identified.

For purposes of evaluating the products obtained and described by the present disclosure as well as the invention herein, several tests were used to characterize the desirable fibrous wood pulp end-use performance improvements resulting from use of the presently disclosed softening agent treatment, and to describe some of the analytical properties of the pulp products. A summary of these tests and definitions follows:

"Pulp 1" is an untreated southern pine kraft pulp sold by Rainier Inc. for use in applications requiring high absorbency.

"Pulp 2" is a southern pine kraft pulp which has been treated with softener triacetin of the present invention.

"Pulp 3" is a southern pine kraft pulp which has been treated with softener triethyl citrate of the present invention.

"Pulp 4" is a cold caustic treated, mercerized fiber available from Rayonier Inc.

"Pulp 5" is a southern pine kraft pulp available from Rayonier Inc. which has been treated with a cationic (quaternary ammonium salt) debonder.

"Pulp 6" is a southern pine kraft pulp which has been treated with softener tri-n-butyl citrate of the present invention.

Several experiments were conducted to demonstrate the effects of triacetin on the aforementioned debonding and absorbency properties of wood pulp, and on absorbent cores made therefrom.

The absorbent cores were generated using the bench scale dry forming system. The bench-scale dry-forming system (BSDFS) is used to produce 12-inch diameter absorbent cores. This system allows the user to vary the number of layers, amount of superabsorbent polymer (SAP), pulp type and content, basis weight and density of the absorbent cores formed. The BSDFS can be used to produce multi-layered air-laid handsheets and mimics a large-scale air-laid pilot plant. The system comprises of a KAMAS CELL™ to defiberize the pulp, a 100-mesh, 12" forming wire in a vacuum forming head, a SAP dosing system, compaction roll for initial densification of web and a heated press for final densification and bonding. The absorbent cores used herein comprised four layers: a bottom layer of tissue, followed by two layers of pulp and SAP, and a final top layer of pulp. The tissue utilized was Tissue Grade 3008, available from Cellu Tissue Corporation of East Hartford, Connecticut. The SAP utilized was in the form of particles sold under the designation No. 7440, available from Stockhausen GmbH of Krefeld, Germany.

Gurley stiffness was measured using 3.5"×1" strips. Radial wicking tests were carried out on 2" circular pads using a Gravimetric Absorbency Test System (GATS) instrument.

EXAMPLE 1

Triacetin (available from Eastmann Chemical Co.) was applied to several pulp sheets of Pulp 1 by spraying directly on the sheets (1% oven-dried charge). Pulp sheets thus treated were referred to as Pulp 2. The treated Pulp 2 and non-treated Pulp 1 were combined at different ratios (0, 33%, 66% and 100%) to make air-laid absorbent cores. The cores contained 55% SAP. These cores were tested to obtain a stiffness value on a Gurley Precision Electronic Bending Resistance Tester. The stiffness value indicates the softness of the material, with a lower stiffness value indicating a more soft material.

A decrease in stiffness was observed as the amount of triacetin treated pulp is increased. A control air-laid absorbent core had a stiffness of 980 mg, while the absorbent cores with 100% triacetin treated pulps had a stiffness of 780 mg. Table 1 summarizes this trend.

Suppleness values are derived from the stiffness values, obtained as described above. Suppleness and stiffness are inversely proportional, and a higher suppleness value is more desirable for an absorbent material. To obtain a value for suppleness, stiffness is divided by one thousand, and the resulting number is inverted.

To measure the absorbent capacity and rate of absorbency of absorbent materials, a radial wicking test was performed on Gravimetric Absorbency Test equipment. Maximum capacity is first measured, and then the time to reach 25%, 50% and 75% of saturation is recorded. Radial wicking results provided in Table 2 showed no negative impact on absorbency properties by including triacetin treated pulps, since the absorbent properties of Core A (no added triacetin) were comparable to Core D (having 100% of 1% triacetin treated pulp). Therefore this example shows that at a 1% triacetin charge, the stiffness of absorbent cores can be reduced by 20%.

TABLE 1

| Core[1] | Pulp 2 (%)/Pulp 1 (%) | Stiffness (mg) | Suppleness (1/g) |
|---|---|---|---|
| A | 0/100 | 983 | 1.02 |
| B | 33/66 | 954 | 1.05 |
| C | 66/33 | 768 | 1.30 |
| D | 100/0 | 784 | 1.28 |

[1] = basis weight for each sample was 520 gsm, density 0.3 g/cc.

TABLE 2

Effect of using various ratios of Pulp 1 and triacetin treated Pulp 2 on radial wicking properties of absorbent cores (Density ≅ 0.30 g/cc)

|  | Average |
|---|---|
| Amount of 1% triacetin pulp: 0%, Core A | |
| Maximum Capacity (g/g) | 20.4 |
| T25 (s) | 12.5 |
| T50 (s) | 77.6 |
| T75 (s) | 246.1 |
| Amount of 1% triacetin pulp: 33%, Core B | |
| Maximum Capacity (g/g) | 21.1 |
| T25 (s) | 14.0 |
| T50 (s) | 86.5 |
| T75 (s) | 255.6 |
| Amount of 1% triacetin pulp: 66%, Core C | |
| Maximum Capacity (g/g) | 21.6 |
| T25 (s) | 13.9 |
| T50 (s) | 82.8 |
| T75 (s) | 240.4 |
| Amount of 1% triacetin pulp: 100%, Core D | |
| Maximum Capacity (g/g) | 20.4 |
| T25 (s) | 13.9 |
| T50 (s) | 81.4 |
| T75 (s) | 233.3 |

EXAMPLE 2

A second group of experiments involved determining the effect of density on softness of air-laid absorbent cores. Each core contained 55% SAP. Air-laid absorbent cores were generated from four different pulp grades, and tested according to the following procedure. Typically, absorbent cores made in the lab have a density of approximately 0.3 g/cc. To achieve greater density, a flat press was used to lower thickness, thereby increasing density. Pressed samples were tested for stiffness. The flat press was also used to compress radial wicking samples from the cores to around 0.39 g/cc to simulate production run densities. As indicated in Table 3, density resulted in an increase in stiffness for all the samples studied. Overall the cores containing triacetin treated pulps had a significantly lower stiffness when compared to the samples of Pulp 1. It was also observed that this decrease in stiffness is maintained irrespective of the density.

TABLE 3

Stiffness vs Density

| Sample[1] | % Treatment | Density (g/cc) | Stiffness (mg) | Suppleness (1/g) |
|---|---|---|---|---|
| Pulp 1 | none | 0.327 | 888 | 1.13 |
|  |  | 0.375 | 1043 | 0.96 |
|  |  | 0.431 | 1201 | 0.83 |
| Pulp 4 | none | 0.296 | 496 | 2.02 |
|  |  | 0.341 | 498 | 2.01 |
|  |  | 0.356 | 574 | 1.74 |
| Pulp 5 | 0.25% debonder | 0.301 | 522 | 1.92 |
|  |  | 0.393 | 593 | 1.69 |
|  |  | 0.42 | 695 | 1.44 |
| Pulp 2[2] | 3% triacetin | 0.293 | 482 | 2.07 |
|  |  | 0.368 | 552 | 1.81 |
|  |  | 0.429 | 630 | 1.59 |

[1]= basis weight of 520 gsm
[2]= 3% charge of triacetin on oven-dried pulp

EXAMPLE 3

The effect of varying the amount of triacetin applied to the pulp was tested by applying varying amounts of triacetin to Pulp 1 pulp sheets. The amount of triacetin charged on oven-dried pulp was varied from 0, 1%, 1.5%, 2.0, 3.0%, 5% and 10%. Air-laid absorbent cores were made then made by using these treated pulp sheets. Each core contained 55% SAP. Stiffness of these sheets was then tested according to the procedure described in Example 1.

Increasing the amount of triacetin charge resulted in an overall decrease in stiffness. This trend can be seen in Table 4, which illustrates that nearly a 50% reduction in stiffness was obtained.

TABLE 4

Effects of Amount of Triacetin in Pulp on Stiffness of Absorbent Core[1]

| % Triacetin | Stiffness (mg) | Suppleness (1/g) |
|---|---|---|
| 0 | 888 | 1.13 |
| 1 | 785 | 1.27 |
| 1.5 | 543 | 1.84 |
| 2.0 | 440 | 2.27 |
| 3.1 | 481 | 2.08 |
| 5 | 475 | 2.11 |
| 10 | 430 | 2.33 |

[1]= basis weight of 520 gsm and density of 0.30 g/cc

EXAMPLE 4

In this example, triacetin was sprayed directly onto an absorbent core made using the BSDFS described previously. The absorbent core was made using untreated Pulp 1. Each core contained 55% SAP, and had a basis weight of 520 gsm. The spraying with triacetin was done after the core had been densified to a density of 0.18 (g/cc). After spraying a known quantity of triacetin (in this case 2.5% based on oven-dried pulp in the core), the core was allowed to sit in a temperature-controlled room for 2 hours. After this, the core was densified to a density of 0.3 g/cc and the stiffness was measured.

The result from this experiment is shown in Table 5, which illustrates that spraying triacetin directly on an air-laid absorbent core also results in a reduction in stiffness.

TABLE 5

Effects of Spraying Plasticizer on Formed Absorbent Core

| Sample | Stiffness(mg) | Suppleness (1/g) |
|---|---|---|
| Core made from Pulp 1, no triacetin | 888 | 1.13 |
| Core made from Pulp 1 with 2.5% triacetin added to core | 492 | 2.03 |

EXAMPLE 5

To determine the softening effects of citrate esters, triethyl citrate was applied to Pulp 1 at a 3% oven-dried charge. The treated pulp (Pulp 3) was then utilized to generate air-laid absorbent cores. These cores were tested for stiffness according to the procedure described in Example 1. The results (Table 6) show that triethyl citrate (obtained from Morflex Inc. of Greensboro, Ga.) behaves very similar to triacetin in reducing the stiffness of the absorbent core.

TABLE 6

Effect of Citrate Added to Pulp on Absorbent Core Produced Therefrom

| Sample[1] | Stiffness(mg) | Suppleness (1/g) |
|---|---|---|
| Core made from Pulp 1, no triethyl citrate | 888 | 1.13 |
| Core made from Pulp 3, 3% triethyl citrate added to pulp | 401 | 2.49 |
| Core made from Pulp 2, 3.1% triacetin added to pulp | 481 | 2.08 |

[1]= each sample contained 55% SAP, had a basis weight of 520 gsm and a density of 0.3 g/cc

EXAMPLE 6

To compare the softening ability of citrate esters to triacetin in pulp, the following experiments were performed. The citrate esters were obtained from Morfwex, Inc of Greensboro, N.C.

To apply the additive to the pulp, 12-inch square sheets of Pulp 1 at a basis weight of 640 gsm were weighed and a calculated mass of plasticizer was sprayed evenly across one side of the sheet. Each pulp sheet was placed in a separate bag and allowed to sit overnight. Next, Kamas energy was determined for each sample, in order to characterize the amount of energy required to break a sheet.

The results are provided in Table 7 (low charge of plasticizer) and Table 8 (higher charge of plasticizer). All three of the tested plasticizers reduced Kamas energy by about 35% when compared to the untreated Pulp 1, from 60 to 38 Wh/kg. The leftover half of each pulp sheet from the Kamas energy test was used in the Mullen strength test.

TABLE 7

| Sample | Plasticizer (%) | Kamas Energy (Wh/kg) | Mullen Strength (kPa) |
|---|---|---|---|
| Pulp 1 | 00.0 | 59.76 | 1091.73 |
| Pulp 2 | 0.27 | 53.35 | 896.30 |
| Pulp 2 | 0.52 | 47.00 | 832.80 |
| Pulp 2 | 0.74 | 38.36 | 848.20 |
| Pulp 1 | 0.00 | 59.76 | 1091.73 |
| Pulp 3 | 0.26 | 47.22 | 920.60 |
| Pulp 3 | 0.55 | 44.35 | 845.00 |
| Pulp 3 | 0.74 | 39.12 | 840.80 |
| Pulp 1 | 0.00 | 59.76 | 1091.73 |
| Pulp 6 | 0.27 | 47.09 | 909.60 |
| Pulp 6 | 0.48 | 40.07 | 924.70 |
| Pulp 6 | 0.71 | 41.47 | 871.60 |
| Pulp 6 | 0.99 | 39.10 | 907.70 |
| Pulp 5, 0.25% debonder | — | 44.48 | — |

TABLE 8

| Sample | Plasticizer (%) | Kamas Energy (Wh/kg) | Mullen Strength (kPa) |
|---|---|---|---|
| Pulp 1 | 00.0 | 59.76 | 1091.73 |
| Pulp 2 | 1.03 | 39.18 | 757.17 |
| Pulp 2 | 2.00 | 38.89 | 792.03 |
| Pulp 2 | 3.00 | 35.44 | 706.83 |
| Pulp 1 | 0.00 | 59.76 | 1091.73 |
| Pulp 3 | 1.00 | 39.92 | 834.50 |
| Pulp 3 | 2.02 | 36.97 | 762.43 |
| Pulp 3 | 3.00 | 34.90 | 785.43 |
| Pulp 1 | 0.00 | 59.76 | 1091.73 |
| Pulp 6 | 2.01 | 36.97 | 860.80 |
| Pulp 6 | 2.94 | 36.78 | 825.37 |
| Pulp 5, 0.5% debonder | | 31.14 | |

EXAMPLE 7

The procedure for measuring stiffness and suppleness described in Example 1 was utilized to compare pulps treated in accordance with the present invention to commercially available pulps. Each sample had a basis weight of 320 gsm and contained no SAP. Table 9 illustrates that the cores made with the plasticizer treated pulps had a significantly lower stiffness when compared to the untreated sample. Also the core made with the debonded pulp had comparable stiffness to the cores made with plasticized pulps.

TABLE 9

| | Pulp 1 | Pulp 5 | Pulp 2 |
|---|---|---|---|
| % Treatment | none | 0.25% debonder | 3% triacetin |
| Density (g/cc) | 0.28 | 0.31 | 0.27 |
| Stiffness (mg) | 732 | 291 | 345 |
| Suppleness (g$^{-1}$) | 1.4 | 3.4 | 2.9 |

EXAMPLE 8

Various absorptive materials of the present invention were examined to determine their ability to absorb fluids against a negative hydrostatic pressure gradient, utilizing the following procedure.

Absorbency of the sample is measured at negative hydrostatic pressure, i.e., negative hydrostatic head. The negative hydrostatic pressure exerts a suction force on the sample. The absorbent material needs to have enough positive force to overcome the negative suction force in order to absorb fluid. The positive force results from the capillary pressure of the fiber. As the absorbent material picks up fluid, the positive pressure decreases. A point is reached when the positive force necessary to counter-balance the suction force insufficient. This point is referred to as equilibrium absorbency and represents the cessation of absorption. The hydrostatic pressure is systematically increased from 3 mm to 45 cm of water, and the equilibrium absorbency at the 40 cm hydrostatic tension value is measured. At a hydrostatic tension value of about 3 mm of water, the fiber network is completely saturated with the test fluid. At the hydrostatic tension value of about 40 cm of water the maximum retention is measured. The confining load on the sample was 0.05 psi, to ensure contact between the sample and test cell.

A schematic illustration of an instrument used to obtain measurements for this characterization is described in U.S. Pat. No. 5,916,670. The instrument comprises a fluid source as well as an adjustable sample compartment. The fluid source comprises a constant-level fluid reservoir in conjunction with a supply reservoir. The entire fluid reservoir component is placed on a balance to allow for determination of the mass of the fluid lost or gained by the fluid reservoir. The fluid source is connected via a tube to the adjustable sample compartment. The adjustable single port compartment (available from M-K Systems of Danvers, Mass.) comprises a solid support on which is placed a filter paper (Whatman #5) and a sample of absorbent material. The solid support mechanism together with the filter and sample are attached to a device which allows for raising and lowering of the sample height relative to the height of the fluid in the fluid reservoir. When the level of the sample in the sample compartment is the same as the level of the constant level fluid reservoir, there is no hydrostatic pressure head applied to the sample. As the sample level is raised above the level of fluid in the constant level reservoir, a negative hydrostatic pressure head is applied to the sample. The magnitude of the hydrostatic pressure head is equal to the difference in height between the sample and the fluid reservoir as measured in centimeters.

Following the procedure described above, the various samples of absorptive material were placed in the instrument and fluid absorption was measured over a range of hydrostatic pressures. Each sample had a basis weight of 320 gsm and contained no SAP. The equilibrium absorbency at the highest negative hydrostatic head was reported as Retention in g/g in Table 10.

The cores made with the debonded pulp had a significantly lower retention when compared to the untreated and plasticized samples. Therefore the cores made with plasticized pulps have a significantly lower stiffness without any negative impact on absorbent properties, unlike the cores made with the debonded pulps.

TABLE 10

| | Pulp 1 | Pulp 5 | Pulp 2 | Pulp 3 |
|---|---|---|---|---|
| % Treatment | None | 0.25% Debonder | 3% Triacetin | 3% Triethyl Citrate |
| Density (g/cc) | 0.17 | 0.18 | 0.17 | 0.15 |
| Retention (g/g) | 3.93 | 1.94 | 3.56 | 3.76 |

EXAMPLE 9

Wicking properties of the material were measured using a GATS system manufactured by M/K Systems of Danvers, Mass. to determine the values for 45° wicking. The set up of the test is described in detail in U.S. Pat. No. 5,916,670, hereby incorporated by reference. A 45° wicking test cell is attached to the absorption measurement device. The test cell essentially consists of a circular fluid supply unit for the test sample and 45° ramps. The fluid supply unit has a rectangular trough and liquid level is maintained at the constant height by the measuring unit.

To perform the test, a sample of the absorbent material to be characterized having dimension of 1"×12" was prepared. The sample was marked every inch along the length of the sample. The sample was then placed on the ramp of the test cell ensuring that one of the edges of the sample dips into the trough. The test was conducted for thirty minutes, after which time the sample was removed and cut along the marked distances. The cut pieces were placed into preweighed aluminum weighing dishes. The weighing dish, containing wet samples, was weighed again and then oven-dried to a constant weight. By conducting a proper mass balance on the data, absorbency of the sample was determined at every inch. For each sample, the amount of fluid absorbed per gram of sample was plotted against distance from the origin (source of fluid). The area under the curve was calculated using the following formula:

$$[(y_1)(x_2-x_1)+0.5(y_2-y_1)(x_2-x_1)+(y_2)(x_3-x_2)+\\0.5(y_3-y_2)(x_3-x_2)+ \ldots +(y_n)\ x_n-x_{n-1})+\\0.5(y_n-y_{n-1})\ (x_n-x_{n-1})],$$

where $X_i$ is distance at the $i^{th}$ inch and $Y_i$ is absorbency at the $i^{th}$ inch.

This area was then multiplied by the gravitational constant (981 cm/s$^2$) and the sine of 45° to result in the work value of ergs/g. A higher value for 45° wicking energy indicates greater absorbency. The total amount of liquid absorbed by the strip divided by the weight of the strip gives the efficiency in g/g.

Each sample had a basis weight of 320 gsm and contained no SAP. Table 11 shows that the cores made with the debonded pulp had significantly lower wicking properties when compared to the untreated and plasticized samples. Thus the cores made with plasticized pulps have a significantly lower stiffness without any negative impact on 45° wicking, unlike the cores made with the debonded pulps.

TABLE 11

|  | Pulp 1 | Pulp 5 | Pulp 5 | Pulp 2 | Pulp 3 |
| --- | --- | --- | --- | --- | --- |
| % Treatment | None | 0.25% Debonder | 0.5% Debonder | 3% Triacetin | 3% Triethyl citrate |
| Density (g/cc) | 0.37 | 0.36 | 0.36 | 0.33 | 0.33 |
| Efficiency (g/g) | 3.7 | 1.6 | 1.56 | 4.0 | 3.1 |
| Energy (ergs/g) | 67752 | 35359 | 31463 | 65926 | 42226 |

EXAMPLE 10

GATS Radical Wicking was carried out on the above samples in accordance with the procedure described in Example 1 to determine the rate of absorbency for each sample and to determine whether there were any differences between the cores made using the plasticizer treated pulps and debonded pulps. Each sample had a basis weight of 320 gsm and contained no SAP. The results are presented in Table 12, which shows that the absorbent cores formed using plasticizer-treated pulps have a better rate of absorbency than the cores formed using debonded pulps.

TABLE 12

|  | Pulp 1 | Pulp 5 | Pulp 5 | Pulp 2 | Pulp 3 |
| --- | --- | --- | --- | --- | --- |
| % Treatment | None | 0.25% Debonder | 0.5% Debonder | 3% Triacetin | 3% Triethyl citrate |
| Density (g/cc) | 0.18 | 0.20 | 0.19 | 0.20 | 0.20 |
| T25 (s) | 4.1 | 7.5 | 6.3 | 4.4 | 3.2 |
| T50 (s) | 9.7 | 17.5 | 15.7 | 10.6 | 10.2 |
| T75 (s) | 17.7 | 29.1 | 29.0 | 18.5 | 18.4 |

EXAMPLE 11

To compare the use of triacetin of the present invention to conventional additives which combine triacetin and cellulose acetate to achieve a different type of material, the following experiment was performed. Absorbent cores were made using cellulose acetate (CA) and triacetin in combination with Pulp 1. The CA fibers (1½", 1.8 Denier) were obtained from Eastman Chemical Company. All cores were made at 520 gsm with 55% SAP. The control sample did not contain any CA and triacetin. In Core 1, the fiber make-up comprised of 92% Pulp 1 and 8% CA fibers. In Core 2, the fiber make-up comprised of 89% Pulp 1, 8% CA fibers and 3% Triacetin. Core 3 was an absorbent core was also made with Pulp 2 (treated with 3% triacetin). The absorbent cores tested were comprised of a tissue layer at the bottom, followed by two layers of pulp and SAP and then a top layer of fluff pulp. In the treated samples, CA and triacetin were added to the bottom two layers. The CA fibers were added through the hammer mill along with the wood pulp. In Core 2, the triacetin was sprayed on to the absorbent core after addition of the CA fibers. The samples so formed were evaluated using the GATS 45° Wicking test procedure described in Example 9.

Table 13 shows that, using CA in combination with triacetin in the formation of an absorbent core results in a negative impact on absorbent properties. On the other hand, Core 3 made with just the triacetin treated pulp of the present invention, did not show any negative impact on absorbent properties when compared to control sample.

TABLE 13

|  | Control | Core 1 (With CA) | Core 2 (With CA + triacetin) | Core 3 (With 3% triacetin) |
| --- | --- | --- | --- | --- |
| Density (g/cc) | 0.4 | 0.4 | 0.4 | 0.39 |
| Efficiency (g/g) | 8.1 | 7.8 | 7.5 | 8.2 |
| Energy (ergs/g) | 119095 | 107365 | 110000 | 122000 |

EXAMPLE 12

Absorbent cores were generated using the air-laid process at a pilot facility, and various pulps, treated as indicated in Table 14. The air-laid system consisted of two forming heads. In the first forming head a mixture of pulp and SAP was added whereas in the second forming head only pulp was added. After air-laying the pulp and SAP on the carrier layer (comprising of a tissue) the resultant web was heat calendered to achieve the target density. Resultant cores had a total amount of SAP of 40%, and the target basis weight of the absorbent core and tissue was 400 gsm.

Gurley stiffness measurements were carried out on the absorbent cores generated using these pulp samples, following the procedure described in Example 1. The results of Table 14 indicate that use of plasticizer in treated pulps can result in a substantial decrease in the stiffness of the absorbent cores. Similar decreases in stiffness can also be obtained by using pulps treated with debonders.

The 45° wicking energy values were obtained according to the procedure described in Example 9. The normalized wicking energy values in Table 15 were calculated by dividing the 45° wicking energy values by the percentage of superabsorbent polymer present in the absorbent core. The results of Table 15 illustrate that cores containing plasticizer-treated pulps exhibit a significantly better wicking performance than cores containing debonder-treated pulps. Also, the wicking performance of some of the absorbent cores containing plasticized pulps is comparable to the cores containing untreated pulps.

TABLE 14

| Sample ID | Pulp | Pulp Treatment | Density (g/cc) | Stiffness (mg) | Suppleness (1/g) |
|---|---|---|---|---|---|
| Sample A | 1 | none | 0.29 | 803 | 1.24 |
| Sample B | 4 | caustic-treated | 0.28 | 511 | 1.90 |
| Sample C | 2 | 1% triacetin | 0.32 | 583 | 1.72 |
| Sample D | 2 | 3% triacetin | 0.30 | 448 | 2.23 |
| Sample E | 3 | 1% triethyl citrate | 0.30 | 442 | 2.26 |
| Sample F | 7 | 1% acetyl triethyl citrate | 0.31 | 390 | 2.56 |
| Sample G | 5 | 0.25% debonder | 0.32 | 513 | 1.95 |

TABLE 15

| Sample ID | Pulp | Pulp Treatment | Density (g/cc) | 45° Wicking energy (ergs/g) | Normalized Wicking energy (ergs/g) |
|---|---|---|---|---|---|
| Sample A | 1 | none | 0.29 | 142614 | 3565 |
| Sample B | 4 | Caustic treated | 0.28 | 112559 | 2814 |
| Sample C | 2 | 1% triacetin | 0.32 | 134064 | 3352 |
| Sample D | 2 | 3% triacetin | 0.30 | 112260 | 2807 |
| Sample E | 3 | 1% triethyl citrate | 0.30 | 97518 | 2438 |
| Sample F | 7 | 1% acetyl triethyl citrate | 0.31 | 98728 | 2469 |
| Sample G | 5 | 0.25% debonder | 0.32 | 81510 | 2038 |

EXAMPLE 13

Absorbent cores were generated using the air-laid process at a commercial scale machine facility under the following conditions: The air-laid system consisted of three forming heads. In the first two forming heads a mixture of pulp and SAP was added whereas in the third forming head only pulp was added. After air-laying the pulp and SAP on the carrier layer (comprising of a tissue) the resultant web was heat calendered to achieve the target density. Resultant cores had a total amount of SAP of 55%, and the target basis weight of the absorbent core and tissue was 500 gsm.

Gurley stiffness measurements were carried out on the absorbent cores generated using these pulp samples, following the procedure described in Example 1.

The 45° wicking energy values were obtained according to the procedure described in Example 9. The normalized wicking energy values in Table 17 were calculated by dividing the 45° wicking energy values by the percentage of superabsorbent polymer present in the absorbent core. The results in Table 17 illustrate that cores formed from plasticizer-treated pulps have comparable wicking performance to cores formed from untreated pulps.

TABLE 16

| Sample ID | Pulp Treatment | Basis Weight (gsm) | Density (g/cc) | Stiffness (mg) | Suppleness (1/g) |
|---|---|---|---|---|---|
| Sample H | 83% pulp 1 and 17% pulp 4 | 515 | 0.36 | 1053 | 0.95 |
| Sample I | 100% pulp 2 containing 1% triacetin | 504 | 0.35 | 625 | 1.6 |
| Sample J | 83% pulp 2 containing 1% triacetin and 17% pulp 1 | 538 | 0.37 | 660 | 1.51 |

TABLE 17

| Sample ID | Pulp Treatment | Basis Weight (gsm) | Density (g/cc) | 45° Wicking energy (ergs/g) | Normalized Wicking energy (ergs/g) |
|---|---|---|---|---|---|
| Sample H | 83% pulp 1 and 17% pulp 4 | 515 | 0.36 | 158356 | 2879 |
| Sample I | 100% pulp 2 containing 1% triacetin | 504 | 0.34 | 134773 | 2450 |
| Sample J | 83% pulp 2 containing 1% triacetin and 17% pulp 1 | 538 | 0.33 | 130044 | 2364 |

EXAMPLE 14

Absorbent cores were generated using the air-laid process at a commercial scale machine facility under the following conditions: The air-laid system consisted of three forming heads. In the first two forming heads a mixture of pulp and SAP was added whereas in the third forming head only pulp was added. After air-laying the pulp and SAP on the carrier layer (comprising of a tissue) the resultant web was heat calendered to achieve the target density. Resultant cores had a total amount of SAP of 30%, and the target basis weight of the absorbent core and tissue was 200 gsm.

The results of Table 18 illustrate that cores formed from plasticizer-treated pulps have comparable wicking performance to cores formed from untreated pulps.

TABLE 18

| Sample ID | Pulp Treatment | Basis Weight (gsm) | Density (g/cc) | 45° Wicking energy (ergs/g) | Normalized Wicking energy (ergs/g) |
|---|---|---|---|---|---|
| Sample K | 83% pulp 1 and 17% pulp 4 | 203 | 0.30 | 110046 | 3668 |

TABLE 18-continued

| Sample ID | Pulp Treatment | Basis Weight (gsm) | Density (g/cc) | 45° Wicking energy (ergs/g) | Normalized Wicking energy (ergs/g) |
|---|---|---|---|---|---|
| Sample L | 100% pulp 2 containing 1% triacetin | 215 | 0.31 | 101229 | 3374 |
| Sample M | 83% pulp 2 containing 1% triacetin and 17% pulp 1 | 211 | 0.29 | 106015 | 3534 |

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims.

We claim:

1. A wood pulp sheet comprising:
   from about 90 weight percent to about 99.9 weight percent of cellulosic fibers; and,
      from about 0.1 weight percent to about 10 weight percent of at least one citrate
   wherein said sheet has a defiberization energy of from about 35 to about 60 Wh/kg.

2. The sheet of claim 1 wherein said citrate is of the formula

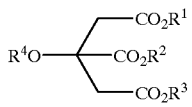

wherein $R^1$, $R^2$ and $R^3$ are each independently alkyl groups, and
   $R^4$ is selected from the group consisting of hydrogen, alkyl groups and $—C(O)R^5$,
      wherein $R^5$ is an alkyl group.

3. An absorbent core comprising from 0.1% to 10% of at least one non-ionic plasticizer.

4. The core of claim 3 wherein said plasticizer is a citrate or triacetin.

5. The core of claim 3 having a suppleness of greater than about $0.7\ g^{-1}$.

6. The core of claim 3 having a density of from about 0.25 g/cc to about 0.5 g/cc.

7. The core of claim 3 having a basis weight of from about 200 g/m² to about 550 g/m².

8. An absorbent core comprising:
   from about 90 weight percent to about 99.9 weight percent of cellulosic fibers; and,
   from about 0.1 weight percent to about 10 weight percent of at least one citrate
wherein said core has a suppleness of greater than about $0.7\ g^{-1}$; a density of from about 0.25 g/cc to about 0.5 g/cc and a basis weight of from about 200 g/m² to about 550 g/m².

9. The core of claim 8 wherein said citrate is of the formula

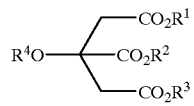

wherein $R^1$, $R^2$ and $R^3$ are each independently alkyl groups, and
   $R^4$ is selected from the group consisting of hydrogen, alkyl groups and $—C(O)R^5$,
      wherein $R^5$ is an alkyl group.

10. The core of claim 8 wherein said core has a wicking energy greater than about 40,000 ergs/g.

11. The core of claim 8 wherein said core has a wicking energy greater than about 60,000 ergs/g.

12. An absorbent core comprising:
   from about 30 weight percent to about 90 weight percent of cellulosic fibers; from about 9.99 weight percent to about 60 weight percent of superabsorbent polymer; from about 0.1 weight percent to about 10 weight percent of at least one non-ionic plasticizer; wherein said core has a suppleness of greater than about $0.7\ g^{-1}$; a density of from about 0.25 g/cc to about 0.5 g/cc and a basis weight of from about 200 g/m² to about 550 g/m².

13. The core of claim 12 wherein said plasticizer is selected from the group consisting of esters and ethers.

14. The core of claim 13 wherein said ethers are glycol derivatives.

15. The core of claim 14 wherein said glycol derivatives are selected from the group consisting of alkyl ethers of low molecular weight glycols and aryl ethers of low molecular weight glycols.

16. The core of claim 13 wherein said esters are selected from the group consisting of formic esters of low molecular weight glycols, ethanoic esters of low molecular weight glycols, propanoic esters of low molecular weight glycols and citrates.

17. The core of claim 13 wherein said plasticizer is triacetin.

18. The core of claim 16 wherein said citrates are of the formula

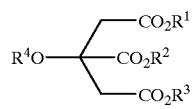

wherein $R^1$, $R^2$ and $R^3$ are each independently alkyl groups, and
   $R^4$ is selected from the group consisting of hydrogen, alkyl groups and $—C(O)R^5$,
      wherein $R^5$ is an alkyl group.

19. The core of claim 12 wherein said cellulosic fibers are derived from at least one type of pulp sheet.

20. The core of claim 12 wherein said cellulosic fibers are derived from a mixture of at least two types of pulp sheets.

21. The core of claim 12 wherein said core has a normalized wicking energy greater than about 2,300 ergs/g.

22. A method for manufacturing a softened absorbent material from cellulosic fibers comprising the steps of:
   a) defiberizing cellulosic fibers to form defiberized cellulosic fibers;

b) blending said defiberized cellulosic fibers with superabsorbent material to form a blended material;

c) depositing said blended material onto a carrier layer under vacuum to form a layered absorbent web; and d) compressing said web to form an absorbent material, wherein an effective softening amount of at least one nonionic plasticizer is added to at least one of said cellulosic fibers, said defiberized cellulosic fibers, said blended material, said web and said absorbent material.

23. The method of claim 22 wherein said absorbent material is an absorbent core.

24. The method of claim 22 wherein said plasticizer is anti-microbial and said softened absorbent wood pulp product is an anti-microbial, softened, absorbent wood pulp product.

25. The method of claim 22 wherein said plasticizer is odor-preventing and said softened absorbent wood pulp product is an odor-preventing, softened absorbent wood pulp product.

26. The method of claim 22 wherein said plasticizer is selected from the group consisting of esters and ethers.

27. The method of claim 26 wherein said ethers are glycol derivatives.

28. The method of claim 27 wherein said glycol derivatives are selected from the group consisting of alkyl ethers of low molecular weight glycols and aryl ethers of low molecular weight glycols.

29. The method of claim 26 wherein said esters are selected from the group consisting of formic esters of low molecular weight glycols, ethanoic esters of low molecular weight glycols, propanoic esters of low molecular weight glycols and citrates.

30. The method of claim 22 wherein said plasticizer is triacetin.

31. The method of claim 29 wherein said citrates are of the formula

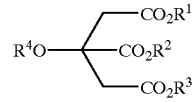

wherein $R^1$, $R^2$ and $R^3$ are each independently alkyl groups, and $R^4$ is selected from the group consisting of hydrogen, alkyl groups and $-C(O)R^5$,
wherein $R^5$ is an alkyl group.

32. The method of claim 22 wherein said cellulosic fibers are derived from at least one type of pulp sheet.

33. The method of claim 32 wherein said cellulosic fibers are derived from a mixture of at least two types of pulp sheets.

34. A method for softening wood pulp sheets comprising the step of adding to said sheets an effective wood pulp sheet softening amount of at least one citrate of the formula

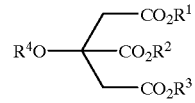

wherein $R^1$, $R^2$ and $R^3$ are each independently alkyl groups, and $R^4$ is selected from the group consisting of hydrogen, alkyl groups and $-C(O)R^5$,
wherein $R^5$ is an alkyl group.

* * * * *